United States Patent [19]

Park

[11] Patent Number: 5,128,325

[45] Date of Patent: Jul. 7, 1992

[54] COMPOSITION COMPRISING MONOSODIUM GLUTAMATE FOR USE IN RELIEVING FATIGUE

[75] Inventor: Sang C. Park, Seoul, Rep. of Korea

[73] Assignee: Miwon Co., Ltd., Seoul, Rep. of Korea

[21] Appl. No.: 796,925

[22] Filed: Nov. 22, 1991

Related U.S. Application Data

[63] Continuation of Ser. No. 448,507, Dec. 11, 1989, abandoned.

[51] Int. Cl.⁵ .................. A61K 31/715; A61K 31/195
[52] U.S. Cl. ........................................ 514/53; 514/561
[58] Field of Search ................... 514/53, 23, 561, 566

[56] References Cited

U.S. PATENT DOCUMENTS

| | | | |
|---|---|---|---|
| 1,602,958 | 10/1926 | Woo | 426/650 |
| 4,481,133 | 11/1984 | Gonzenbach et al. | 424/49 |
| 4,687,782 | 8/1987 | Brantman | 514/561 |
| 4,741,914 | 5/1988 | Kimizuka et al. | 426/650 |

OTHER PUBLICATIONS

Chem. Abstracts 101(17): 150240w Shiotsubo (1984).

Primary Examiner—Frederick E. Waddell
Assistant Examiner—Raymond J. Henley, III
Attorney, Agent, or Firm—Birch, Stewart, Kolasch & Birch

[57] ABSTRACT

A method for relieving fatigue in a mammalian recipient by administering to the mammalian recipient an effective amount of monosodium L-glutamate or a health food composition thereof.

2 Claims, 1 Drawing Sheet

COMPOSITION COMPRISING MONOSODIUM GLUTAMATE FOR USE IN RELIEVING FATIGUE

This application is a continuation of application Ser. No. 07/448,507, filed on Dec. 11,1989, now abandoned.

BACKGROUND OF THE INVENTION

1. Field of the Invention

The present invention relates to a composition comprising monosodium L-glutamate (hereinafter "MSG") and more particularly, to a composition comprising MSG for use in adding to foods, food additives, soft drinks, vitamins, and a method of administering of 0.01 g to 0.4 g/kg/day of MSG to a human in relieving fatigue, especially from muscle exercise (hereinafter "fatigue").

2. Description of the Prior Art

There are many types of known MSG obtained from natural substances or synthetic methods. It has been previously disclosed in the art that such MSG is widely used as a seasoning agent with a small amount thereof. However, such MSG is unknown to relieve fatigue by administering a large amount thereof to a human.

SUMMARY OF THE INVENTION

Accordingly, it is an object of the present invention to provide a composition comprising MSG for use in adding to foods, food additives, soft drinks, vitamins, or the like so as to relieve fatigue.

Another object of the present invention is to provide drink composition comprising MSG for use in relieving fatigue.

A further object of the present invention is to provide a method of administering of 0.01 g to 0.4 g/kg/day of MSG to a human in relieving fatigue.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF PREFERRED EMBODIMENTS

Figure 1:
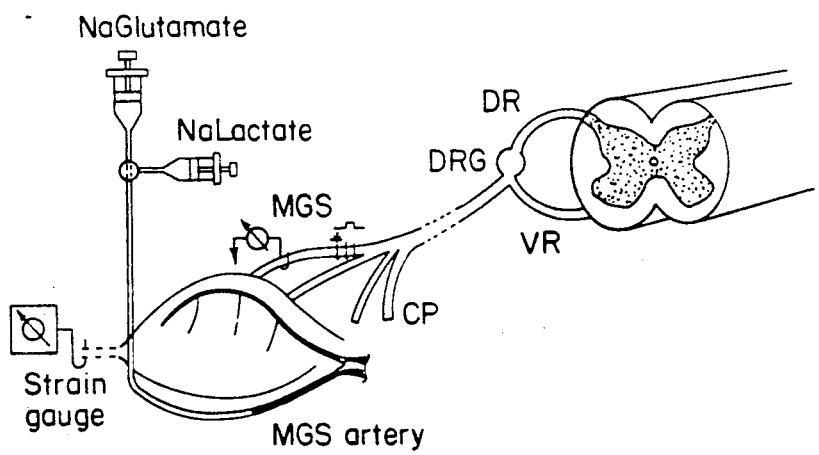
FIG. 1 diagrammatically shows that MSG according to the present invention acts Medical Gastrocnemius Nerve (hereinafter "MGN")

Referring now in detail to the present invention, there is provided a composition for use as a relieving agent of fatigue, the composition comprising MSG with a large amount thereof in foods such as Aspartates, Bean sprouts, food additives, soft drinks, vitamins, or the like.

The present invention is a method of relieving fatigue in a mammalian recipient by administrating to the mammalian recipient about 0.01 g to 0.4 g/kg/day of the free MSG or a food composition thereof. The rate is based on whole body mass.

In order for the MSG to have maximum effectiveness in relieving fatigue, the MSG should be ingested orally about 30 minutes to 3 hours before strenuous exercise, preferably 30 minutes to 2 hours before the strenuous exercise.

The composition for relieving fatigue of the present invention may take many forms and preferably contains 0.2 to 100 weight %, more preferably 0.2 to 10 weight % MSG and an ingestible solid or liquid ingredient or carrier.

When the composition is a liquid composition such as soup, a soft drink or a health drink, the liquid composition will usually contain 0.2 to 2 weight %, preferably 0.2 to 0.5 weight % of MSG and may also contain 0 to 5 weight %, preferably 1 to 5 weight percent, more preferably 1 to 3 weight percent of a sugar such as sucrose, lactose or glucose and may optionally further contain a mixture of electrolytes such as water-soluble salts of sodium and potassium (e.g., sodium chloride or potassium chloride) in a concentration of 0 to 0.06 M, preferably 0.02 to 0.04 M.

When the composition is in the form of a vitamin tablet, the vitamin tablet will generally contain 0.2 to 50 weight %, more preferably 0.2 to 10 weight % of MSG and the remainder essentially vitamins and a binder for the vitamins.

The following additional optional ingredients may also be added in the indicated amounts.

| Ingredient | Usual Content | Preferred Content |
| --- | --- | --- |
| Amino acids | 0-100 wt. % | 0.5-20 wt. % |
| Artificial flavoring agents | q.s. | q.s. |
| Natural flavoring agents | q.s. | q.s. |
| Coloring agents | q.s. | q.s. |

*q.s. = quantum sufficit

The present invention is to provide the possibility of in vivo modulation of lactate accumulation during the strenuous exercise. Since the generation of lactate during exercise seems to be inevitable and to be linked with the fatigue generation with the consequent loss of exercise efficiency, it is very important to develop the measure to escape the lactate generation or to decrease lactate accumulation during the work load without functional loss.

The oxygen debt in the exercising muscle limits the flow of lactate to citric acid cycle and turns lactate to pyruvate and pyruvate to alanine. Therefore, the possibility of in vivo modulation of lactate accumulation during the work load lies in development of any method to increase the turnover of pyruvate to alanine and lactate to pyruvate. For the purpose, it is designed to increase the glutamate concentration in the muscle tissues in order to stimulate the turnover of pyruvate to alanine via transamination reaction, through which it is assumed that the lactate accumulation during exercise could be reduced and there would follow the reduction of fatigue generating and the improvement of exercise efficiency.

The fatigue generation after prolonged exercise is related with lactate accumulating in the muscle tissues by the relative anaerobic glycolysis for energy generation due to relative shortness of oxygen supply. The accumulated lactate causes a decrease in pH of the tissues, the impairment of Na+ K+ pump and other metabolic activities, and fatigue generation. Therefore, it may be expected that the exercise fatigueness could be adjustable, if any measure which can modulate the lactate level in vivo can be available. The lactate is converted to pyruvate by lactate dehydrogenase (hereinafter "LDH") and pyruvate is either turned over to acetyl CoA by pyruvate dehydrogenase (hereinafter "PDH") complex or transaminated by glutamate pyruvate transaminase (hereinafter "GPT"). Due to the relative lack of oxygen supply to the exercising muscles during exercise, the turnover of pyruvate by PDH complex is limited, but its turnover by GPT becomes the major activated pathway.

Furthermore, both enzymes of LDH and GPT are rich in the tissues and of the equilibrium characters, which provide the possibility of in vivo modulation of lactate through the simple mass ratio of reactants. That is, the increased turnover of pyruvate into alanine can be induced by the increase of glutamate in the muscle tissues and the resulting lowering of pyruvate might cause the lactate turnover into pyruvate secondarily. Actually among the various tissues, the concentration of glutamate is most highest in the muscle tissues, and among amino acids composition in the blood, the muscle veins are richest in the contents of alanine and glutamine.

The experimental animals, Sprague-Dawley rats, are divided into non-trained and trained groups. For the trained groups, the animals are loaded with swimming exercise in the warm of about 30°-33° C. and wavy water with 10 g of a weight member attached on the tail for 5 minutes per day. After 4 weeks of training, the trained and untrained rats are treated either with MSG solution or with control saline solution intragastrically in varying doses. These rats are subject to the test of exercise efficiency such as prolongation of survival in the water and to the varying biochemical determination, focused on the change of lactate accumulation in the muscle tissues by exercise. In order to elucidate the metabolic turnover of lactate, activity monitoring of LDH and GPT as well as the content determination of lactate, alanine, glutamate and glutamine in the muscle tissues, liver tissues and blood may be carried out.

Accordingly, if it turns out to be possible to modulate the lactate accumulation in the exercising muscles in vivo by supply of MSG without any functional loss or rather with improvement of exercising efficiency, the prospect in the application of the results of the present study is tremendous.

It is confirmed that the effect of lactate accumulation is related to the exercise efficiency;

determined that the effect of training decides lactate accumulation in the exercising muscles;

monitored that the enzymatic changes of LDH and GPT is to be induced in the exercising muscle tissues by training;

evaluated that the effect of glutamate uptake is to decrease the level of lactate accumulating in the exercising muscles, monitored that the effect of glutamate is to increase the exercise efficiency; and compared that the effect of glutamate depends on training and biochemical changes of the exercising muscles, liver tissues and blood.

TEST EXAMPLE 1

Swimming Exercise Test of Animals

1) Experimental materials

Kits for measuring lactate, LDH, GPT, and glutamate oxaloacetate transaminase (hereinafter "GOT") were made in Sigma Co., St. Louis, Mo, U.S.A. MSG and sodium aspartate were from Miwon Co., Seoul, Republic of Korea. Experimental Sprague-Dawley rats were from animal breeding form of Seoul National University, Seoul, Republic of Korea. Other reagents were of analytical grade of commercial products in the market.

2) Swimming acceptable training of animals

Many Sprague-Dawley white rats were loaded with swimming exercise in the warm (30° C.) and wavy water, a circular water tank, who have 10 g of a weight metal member attached on the tail thereof, respectively, for 5 minutes a day for soaking into the water and preventing the experimental rats from utilizing floating forces. The water tank has about 1 m of a depth and about 1 m of a diameter thereof (Baker & Horvath (1964), Flaim et al (1979)).

3) Division of experimental group

The experimental rats mastered the training were divided to an experimental group of 10 rats at random such as a pair of MSG groups (a 40 mg/head group and a 80 mg/head group), an aspartate group (40 mg/head group), and a control group (saline group). Before exercises, amino acid solution was injected into an abdominal cavity thereof, respectively.

4) Determination of swimming period time

After 30 minutes from the administration of amino acid solution to the initial trained experimental rats, the rats were trained again under same conditions of the swimming acceptable training step. At this time, the experimental rats were divided to a group which mastered the swimming for 10 minutes, and a group which did not survive under the water for 10 minutes after they swimmed repeatedly.

TEST EXAMPLE 2

Biochemical Analysis

1) Experimental material treatment

Blood and femoral muscle and liver tissues were picked out from the experimented rats of Test Example 1. 1 ml of the blood was added to 2 ml of 8% cold perchloric acid in a tube for determining the lactate. Serum separated from the remaining blood was stored a deep freezer at −70° C. Also the femoral muscle and liver tissue were stored the deep freezer at −70° C. The tissues of liver and femoral muscle was pulverized in 10% phosphate buffered saline (PBS) and centrifuged by using a 1.000 centrifugal separator at 4° C. for 15 minutes so as to remove the cellular debris. The removed upper solution were centrifuged by using a 100.000 ultrahigh speed centrifugal separator again so as to separate the cytosol fractions. The supernatants were used as fractions for determining GOT, GPT and LDH. The precipitated were used as microsome fractions for determining gamma glutamyltranspeptidase (GGTP).

2) Lactate content determination

The lactate contents of the blood and tissues were measured by using the Sigma lactate/pyruvate diagnostic kit under the Sigma 826-UV procedure. Generally, nicotinamide adenine dinucleotide (hereinafter "NAD") was reduced when lactate was turned over to pyruvate by the enzyme of LDH. At this time, differences of absorption rate under the conversion of AND to NADH were used at 340nm. In order to minimize the error of measurement, a velocity control was performed by using Sigma metabolite control serum.

3) Enzyme activity determination

The measurement of GOT, GPT, and LDH was performed by corresponding Sigma kit made in Sigma Co., U.S.A. A final object is to determine the activity of GOT and GPT coupled with LDH by checking the increase of the absorption rate at 340nm causing the conversion of AND to NADH produced from the metabolism thereof. On the other hand, the activity of GGTP was calculated by determining the absorption ray rate of p-nitroanilide produced from the enzyme reaction and using the microsome fraction as an experimental material. At this time, gamma-glutamyl-p-nitroanilide and glycylglycine were used as a donor and a receptor of gammaglutamyl, respectively.

4) Ammonia content determination

In order to determine the ammonia content in the experimental material, the Berthelot method was utilized. That is, the color reaction was accomplished by mixing 1 ml of experimental material, 1 ml of phenol reagent (0.125 g of sodium nitroprusside, 25 ml of phenol in 500 ml of distilled water, hereinafter "D.W."), and 1 ml of alkaline hypochlorite reagent (12.5 g of sodium hydroxide, 20 ml of chlorox in 500 ml of D.W.). Thereafter, the ammonia content was determined by the standard curve line at 630nm of an optical density, hereinafter "O.D.".

5) Protein quantitative analysis

Under the protein Lowry method, the experimental material was mixed with a reagent A 2% w/v of sodium carboxylate, 0.1 N sodium hydroxide), and a reagent B (2% w/v sodium tartrate). Thereafter, the phenol reagent was added to the mixture solution so as to achieve the color reaction. After the mixture solution was stored at room temperature for 30 minutes, it was compared of the absorption rate with a standard solution of serum albumin. The protein quantity analysis was accomplished by calculating the results.

TEST EXAMPLE 3

Muscle Contractibility

1) Experimental animal

After cats were put under anesthesia by using pentobarbital sodium 930mg/kg, i.p.), a catheter was inserted into the respiratory conduit and jugular vein thereof. The pressure changes were continuously recorded by connecting a pressure transducer to the catheter and connecting a recording machine to the pressure transducer. The sciatic nerve was appeared by taking out the skin of the left leg and the nerve looked out into the medial gastrocnemius made to appear. The achilles tendon was appeared and cut. The cut end was connected to the pressure transducer so as to record the muscle tension. The removed skin used to make a mineral oil pool. The cat was fixed on a cat fixing apparatus and connected to a warm water circulation device for maintaining a constant temperature for the cat.

2) Lactate concentration change

The Hartmann solution (27 mM/L of lactate concentration) was continuously introduced into the cat though the vein and femoral artery. In order to determine the lactate concentration change, a control saline group, 50 mM/L of lactate concentration group, a 27 mM/L of lactate concentration group, and a 100 mM/L of lactate concentration group.

3) Amino acid solution infusion

The muscle tension of the digastric muscle was recorded with a 30 minutes interval for 1 minute by stimulating the sciatic nerve with the infusion of amino acid solution through the jugular vein. After stopping the infusion of amino acid solution, the muscle tension of the digastric muscle was recorded with a 30 minutes interval.

4) Stimulation and record

An electric stimulation was accomplished by stimulating 10 times of the A & B nerve stimulation value with 0.1 msec stimulation time period, low frequency, and high frequency through the platinum electrode for activating the A nerve fiber of the efferent nerve. The A & B nerve stimulation value was calculated from a compound action potential at the inner digastric muscle after stimulating the sciatic nerve. Signals on the recording electrode were observed at the oscilloscope through an amplifier. The muscle tension of the triceps surae was recorded by stimulating with low frequency and high frequency for 1 minute. Also, the muscle tension of the digastric muscle was recorded by stimulating with a 30 minutes interval under the infusion of a 50 ml of high concentration or a low concentration jugular vein. After stopping the infusion of sodium lactate, the muscle tension of the digastric muscle was recorded for 1 minute with a 30 minutes interval within 1-2 hours.

5) Statistical analysis

All results were treated by analyzing with a paired t-test and a non paired t-test.

TEST EXAMPLE 4

Application to a Human

1) Conditions for treadmill test

Middle distance runners were divided to a control group, a solution A group, and a solution B group. The solution A group was provided with a bean sprouts soup (99, 80%) including sodium chloride (0.20%). On the other hand, the solution B group was provided with a bean sprouts soup (96.55%) including sodium chloride (0.20%), brown sugar (3.00%), aspartate (0.14%), and MSG (0.10%). The solution B group runners took 400ml of solution B before 2 hours from beginning of the exercise. After the runners started to warm up for 3 minutes (200 m/min), run for 3 minutes (280 m/min). Thereafter, the runners rested for 3 minutes and monitored the content of blood lactate and ammonia, and monitored again at 30 minutes and 2 hours from the resting time.

2) Cooking method of bean sprouts soup 1.2 kg of bean sprouts put into 600 ml of water and extracted by a steaming compression. Thereafter, the food additives such as sodium chloride, sugar, aspartate, and MSG were added to the bean sprouts extract for eating as a soup.

RESULTS OF TEST EXAMPLES

1) Exercise efficiency (a) Sprague-Dawley white rats (8 head) who trained for 4 weeks compared with sprague-Dawley white rats (8 head) who did not trained about the survival time as shown in the following Table 1.

TABLE 1

Effect of Training on Survival Time in Swimming Test of Rats

| Groups | Survival Time (min) |
| --- | --- |
| Non-trained group (n = 8) | 8.49 ± 1.11 |
| Trained | 15.42 ± 2.35* |

*$P < 0.01$
All the data means ± a standard deviation, hereinafter "S.D."

Thus, the survival time was 8.49±1.11 minutes about the nontrained group whereas that was 15.42±2.35 minutes about the trained group.

(b) After Sprague-Dawley white rats (5 head made to swim with a 5 minutes interval, the lactate content in the blood thereof the non-trained group was 8.261±2.243 mmol whereas the trained group was 5.490±0.439 mmol as the following Table 2.

TABLE 2

Effect of Training on the Level of Blood Lactate in Rat after Strenuous Exercise

| Groups | Blood Lactate (m mol/L) |
| --- | --- |
| Non-trained (n = 5) | 8.261 ± 2.243 |
| Trained (n = 5) | 5.490 ± 0.439 |

All the data means ± S.D

Thus, the trained group had only 66% of lactate content about that of non-trained group.

(c) In order to compare the lactate clearance in the tissues after overexercise, Sprague-Dawley white rats (4 head) made to swim with a 5 minutes interval and thereafter, the trained group had an amount of lactate content in the blood, that is, 6.414±1.275 mmol/L when compared with 10.188±1.018 mmol/L of the non-trained group as shown in Table 3. Thus, the trained group had 63% of lactate content about that of the non-trained group. Also, after 3 minutes, from the exercise thereof the non-trained groups had 6.736±1.006 mmol/L when compared with 5.190±1.180 mmol/L of the trained group (Table 3). Thus, the lactate content of the trained group was 77% of that of the non-trained group. However, after 30 minutes from the exercise thereof, the trained group had an approximately same amount of lactate content in the blood to the non-trained group.

TABLE 3

Comparison of Changes in Blood Lactate Level of Rats in Recovery Period Following Exercise

| Time after Exercise | Non-trained (n = 4) | Trained (n = 4) |
| --- | --- | --- |
| Resting | 2.104 ± 0.476 | 2.895 ± 1.502 |
| 0 min. | 10.188 ± 1.018 | 6.414 ± 1.275 |
| 3 min. | 6.736 ± 1.006 | 5.190 ± 1.180 |
| 30 min. | 3.211 ± 0.792 | 3.489 ± 1.147 |

All the data means ± S.D. in mmol/L

Thus, the non-trained group appeared to have higher lactate content in the blood thereof than that of trained group within the recovery time period from the exercise thereof.

(d) As shown in table 4, in the activity of LDH, GPT, GOT, and GGPT related to the lactate clearance, LDH and GPT had a tendency to act strongly in the tissues. GOT in the non-trained group had 0.490±0.099 I.U/mg protein whereas that in the trained group had 0.666±0.274 I.U/mg protein. Thus, GOT in the tissues of the trained group increased 36% compared with that of the nontrained group. Thus, MSG effect may be potentiated in the trained recipients for relief from muscular fatigue.

TABLE 4

Effect of Training of Enzymic activities in Rat Skeletal Muscles

| Enzymes | Nontrained (n = 13) | Trained (n = 14) | Test |
| --- | --- | --- | --- |
| LDH | 1.756 ± 0.48 | 1.922 ± 0.576 | |
| GPT | 0.0782 ± 0.0272 | 0.0932 ± 0.039 | |
| GOT | 0.490 ± 0.099 | 0.666 ± 0.274 | $P < 0.05$ |
| GGTP | 1.683 ± 0.877 | 1.463 ± 0.617 | |

All the data means ± S.D. in I.U./mg/protein.

2) Results of MSG or Aspartate Administration (a) Each experimental white rats group (10 head) who trained for 4 weeks was injected into the abdominal cavity thereof with 40 mg of MSG or aspartate dissolved in saline solution, or only saline solution. After 30 minutes from the injection, the survival test in the water was performed. Therefore, the MSG group and aspartate group exhibited 17.1±2.35 minutes and 18.5±5.3 of the survival time, respectively. However, the only saline group exhibited 14.6±4.88 as shown in Table 5.

TABLE 5

Effect of Aminoacid Uptake on Survival Time in Swimming Test of Trained Rats

| Groups | Survival Time (Min) |
| --- | --- |
| Control saline group (n = 5) | 14.6 ± 4.88 |
| Glutamate group (n = 5) | 17.1 ± 2.35 |
| Aspartate group (n = 5) | 18.5 ± 5.3 |

All the data means ± S.D.

(b) The MSG and aspartate groups

Might be extended the survival time. Furthermore, when the 40 mg/head group compared with a 80 mg/head group exhibited 19.6±2.84 of survival time.

TABLE 6

Dose Effect of Glutamate on Survival Time in Swimming Test of the Trained Rats

| Groups | Survival Time (Min) |
| --- | --- |
| Control saline Group (n = 5) | 14.6 ± 4.88 |
| Glutamate group I (40 mg/head) (n = 4) | 17.3 ± 2.85 |
| Glutamate group II (80 mg/head) (n = 4) | 19.6 ± 2.84 |

All the data means ± S.D.

Thus, a large dosage to the experimental rat had a tendency to extend the survival time in the water. Thus the aminoacid such as MSG or aspartate may relieve muscular fatigue.

3) Muscle Contractile Force

Figure 2:
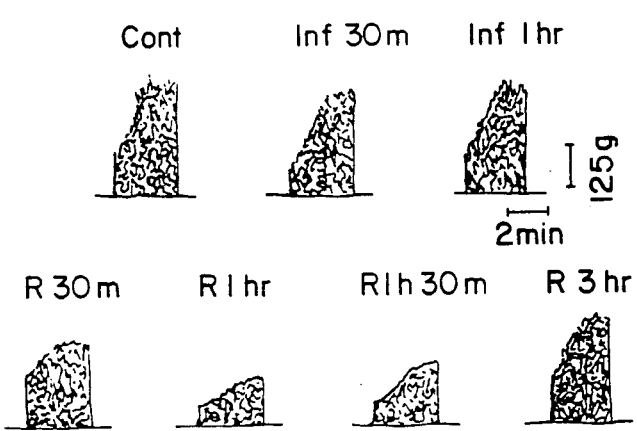
FIG. 2 shows an experimental data of isometric twitch tension during infusion and recovery from 50 mM of sodium lactate.

In order to observe the muscle contractile force according to the lactate accumulation, the cat used as an experimental animal and the pressure transducer attached to the achilles tendon thereof. The contractibility changes of the medical gastrocnemius were measured by stimulating the medial gastrocnemius according to the MSG or lactate concentration to be infused into the sural artery disposed in the muscle (FIG. 1). The stimulation on the inner medial gastrocnemius nerve was electrical with a 2H interval for 1-10 minutes and the contractile force of the inner medial gastrocnemius muscle was measured. The amino acid solution was infused into the cats as a 50 mM of sodium lactate, a 50 mM of MSG, a mixture of 20 mM of MSG and 50 mM of sodium lactate, and a mixture of 20 mM of alanine and 5 mM of sodium lactate. When 50 mM of sodium lactate solution was infused into the rats, the muscle contractile force was gradually reduced (FIG. 2). That is, after infusing the solution into the cats for 1 hour, it was 89.6% at 30 minutes, 74.2% at 1 hour, 59.2% at 1.5 hours, 58.8% at 2 hours, and 40.8% at 3 hours based on 100% at the infusion initiation time as shown in Table 7.

TABLE 8

The Pattern of Aminoacid Released from the Skeletal Muscles

| Aminoacid | Human forearm | Perfused rat hindquarter | Muscle protein |
|---|---|---|---|
| alanine | 28 | 23 | 6.4 |
| glutamine | 23 | 24 | 6.6 |
| aspartate | 0 | 0 | 7 |
| glutamate | 0 | 1.5 | 12 |
| others | 49 | 51.5 | 68 |

Data in percentage from Cahill and Ruderman & Berger.

The enzymes of lactates were increased of its activities by exercise, that is, LDH made to convert lactate to pyruvate, GPT made to convert pyruvate and glutamate to alanine and -ketoglutarate, and GOT made to convert α-ketoglutarate and aspartate to glutamate and

TABLE

Charges in Contractile force during Infusion of and Recovery from Lactate, Glutamate and Alanine

| | Infusion | | Recovery | | | |
|---|---|---|---|---|---|---|
| | 30 min | 1 h | 30 min | 1 h | 1 h 30 min | 2 hs |
| 50 mM Na Lactate | 91.1 3.43 (n = 11) | 90.3 3.46 (n = 7) | 89.6 6.2 (n = 12) | 74.2 9.6 (n = 7) | 59.2 17.4 (n = 2) | 56.8 0.32 (n = 2) |
| 20 mM Na Glutamate mixed with 50 mM Na lactate | 91.7 3.4 (n = 4) | 89.4 3.9 (n = 4) | 95.6 6.7 (n = 4) | 92.7 7.0 (n = 4) | 98.7* 9.8 (n = 2) | 94.9 7.2 (n = 2) |
| 50 mM Na Glutamate | 99.3 3.6 (n = 3) | 95.2 3.4 (n = 2) | 106.1 — (n = 1) | 106.3* 0.1 (n = 2) | 101.8* 2.8 (n = 2) | |
| 20 mM Alanine mixed with 50 mM Na Lactate | 92.5 4.9 (n = 6) | 84.1 10.7 (n = 6) | 80.2 13.8 (n = 6) | 75.1 12.3 (n = 6) | 76.2 15.7 (n = 4) | 77.9 24.2 (n = 3) |

All values Means = S.D.
P < 0.01: significantly different from value of 50 mM Na Lactate.

However, when 50 mM of MSG solution was infused into the cats, there was no change of the muscle contractile force according to the time pass.

Figure 3:
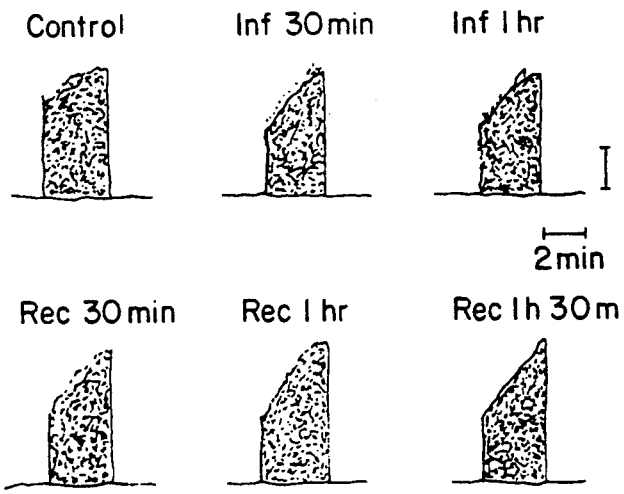
FIG. 3 shows an experimental data of isometric twitch tension infusion and recovery from 20 mM of MSG mixed with 50 mM of sodium lactate.

As shown in FIG. 3, when the mixture solutions of 20 mM of MSG and 50 mM of sodium lactate were infused into the cats, the muscle contractile force was changed a little. That is, it was 95.6% at 30 minutes, 98.7% at 1.5 hours, and 94.9% at 2 hours. When the mixture of 20 mM of alanine and 50 mM of sodium lactate were infused into the cats, it was 84.1% after 1 hour infusion and 80.2% at 30 minutes of recovery. MSG of the present invention may relieve muscular fatigue.

4) Enzyme Efficiency

Table 8 illustrated a pattern of aminoacid released from the skeletal muscles and Table 9 illustrated enzymes of aminoacid metabolism in skeletal muscles through the experimental rats. That is, the exercise might accelerate the enzymes of lactates (Mole et al). Accordingly, in the rat experiments, MSG and aspartate were consumed in the skeletal muscles thereof very fast (Table 8). However, alanine, glutamine, and other amino acids were accumulated in the skeletal muscles thereof after exercising.

oxaloacetate as shown in Table 9. In turn, an inverse reaction of LDH, GPT, and GOT might be performed. Therefore, the increase of anaerobic threshold or lactate threshold in the exercise might mean an increase of those enzyme activities. Accordingly, in the GPT step, an additional glutamate could accelerate the activities of enzymes so that it may accelerate the exercise efficiency. That is, MSG may relieve muscular fatigue.

TABLE 9

Enzymes of Aminoacid Metabolism in Skeletal Muscles

| Enzymes | Activity* | Increases by training |
|---|---|---|
| alanine aminotransferase (GPT) | 46 | + |
| aspartate aminotransferase (GOT) | 200 | + |
| glutamate dehydrogenase (GDH) | 0.011 | + |
| adenylate deaminase (ADA) | 200 | − |

*I.U./g wet muscle tissues.
Data from Male et al., Holloszy et al.

5) Lactate Content in a Human for Recovery Period Time

Table 10 illustrated an effect of aminoacid uptake by observing the lactate content in the blood for recovery period time after treadmill exercise.

TABLE 10

Effect of Aminoacid Uptake on the Blood Lactate in Recovery Period from Treadmill Exercise in a Human (Unit: m mol/l)

| Time after exercise | Control group (n = 10) | Solution A group (n = 20) | Solution B group (n = 20) |
|---|---|---|---|
| Resting | 2.409 ± 0.396 | 2.266 ± 0.627 | 2.013 ± 0.561 |
| 3 min. | 12.012 ± 2.046 | 11.968 ± 1.958 | 9.823 ± 1.947 |
| 30 min. | 6.292 ± 2.684 | 4.829 ± 1.958 | 3.003 ± 0.968 |
| 2 hr. | 2.231 ± 0.495 | 2.277 ± 0.759 | 1.584 ± 0.356 |

All the data are mean ± S.D.

Wherein the runners took 500 ml of solution before 2 hours from exercise start. Thus, the solution B group showed lowest lactate content in the blood of the runners. Because the runners of the solution B group enriched aminoacid such as MSG and aspartate. Accordingly, MSG of the present invention may relieve muscular fatigue.

FORMULATION EXAMPLE 1

Monosodium glutamate is dissolved in a cola syrup such as Coca-Cola ® syrup and the syrup is mixed with carbonated water to form Coca-Cola ® containing 0.3 weight % of MSG. The Coca-Cola ® may be bottled or canned in 12 oz., 16 oz., 1 liter or 2 liter containers.

FORMULATION EXAMPLE 2

3 grams of MSG are added to a 1 liter container of Gatorade ®.

FORMULATION EXAMPLE 3

0.2 grams of MSG are added to a vitamin tablet formulation prior to tableting. MSG is mixed with the vitamin tableting material and vitamin tablets are formed.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A method of reducing the lactate content in the blood of an athlete by a process which comprises feeding the athlete a food composition and a food additive consisting essentially of monosodium glutamate, aspartate, and sugar, from about 30 minutes to about two hours before strenuous exercise.

2. A method of reducing the lactate content in the blood of an athlete according to claim 1 wherein the amount based on the food composition of the monosodium glutamate is 0.10%, of the aspartate is 0.14%, and of the sugar is 3.00%.

* * * * *